(12) United States Patent
Tonami

(10) Patent No.: US 8,497,480 B2
(45) Date of Patent: Jul. 30, 2013

(54) PARTICLE RADIOTHERAPY APPARATUS

(75) Inventor: Hiromichi Tonami, Kyoto-fu (JP)

(73) Assignee: Shimadzu Corporation, Kyoto (JP)

( * ) Notice: Subject to any disclaimer, the term of this patent is extended or adjusted under 35 U.S.C. 154(b) by 238 days.

(21) Appl. No.: 13/133,012

(22) PCT Filed: Dec. 16, 2008

(86) PCT No.: PCT/JP2008/072868
§ 371 (c)(1),
(2), (4) Date: Jun. 6, 2011

(87) PCT Pub. No.: WO2010/070737
PCT Pub. Date: Jun. 24, 2010

(65) Prior Publication Data
US 2011/0240867 A1    Oct. 6, 2011

(51) Int. Cl.
*G01T 1/166* (2006.01)
(52) U.S. Cl.
USPC ............................ 250/363.04; 382/132; 378/4
(58) Field of Classification Search
USPC .......... 250/363.04, 360.1, 361 R, 362, 363.1,
250/363.01–363.09, 390.1, 390.01–390.09,
250/390.11–390.12, 370.1, 370.01–370.09,
250/370.11–370.15; 382/132; 378/4, 13,
378/21, 63, 64, 65
See application file for complete search history.

(56) References Cited

U.S. PATENT DOCUMENTS

| | | | |
|---|---|---|---|
| 7,262,415 B2 * | 8/2007 | Crosetto | 250/363.05 |
| 8,344,326 B2 * | 1/2013 | Amano | 250/363.03 |
| 2005/0109943 A1 * | 5/2005 | Vaquero et al. | 250/363.04 |
| 2007/0023699 A1 * | 2/2007 | Yamashita et al. | 250/492.21 |
| 2010/0128956 A1 * | 5/2010 | Yamaya et al. | 382/132 |
| 2010/0172468 A1 * | 7/2010 | Gregerson | 378/20 |

OTHER PUBLICATIONS

Yamaya et al., Title: A Multiplex "OpenPET" Geometry to Extend Axial FOV without Increasing the Number of Detectors, 2008, IEEE Nuclear Science Symposium Conference Record.*
Yamaya, Taiga et al., "An Initial Investigation of Open PET Geometries", IEEE Nuclear Science Symposium Conference Record, 2007 (USA), No. 5, pp. 3688-3690.

* cited by examiner

*Primary Examiner* — David Porta
*Assistant Examiner* — Taeho Jo
(74) *Attorney, Agent, or Firm* — Cheng Law Group, PLLC

(57) ABSTRACT

In order to provide a particle radiotherapy apparatus with high sensitivity for detecting annihilation radiation pairs, an elliptic detector ring of a particle radiotherapy apparatus according to this invention makes rotating movement relative to a top board. Specifically, with rotation about a base axis of a first ring and a second ring, the elliptic detector ring makes rotating movement in a state of being tilted relative to the first ring. Incidentally, the elliptic detector ring cannot be disposed in a position to interfere with travel of this particle beam. According to the construction of this invention, the elliptic detector ring is tilted relative to the top board, and besides makes rotating movement relative to the top board. Since the elliptic detector ring can be moved away from the particle beam by rotating the elliptic detector ring, it is possible to provide the particle radiotherapy apparatus which can detect annihilation radiation while emitting the particle beam.

9 Claims, 11 Drawing Sheets

Fig. 6
(a)
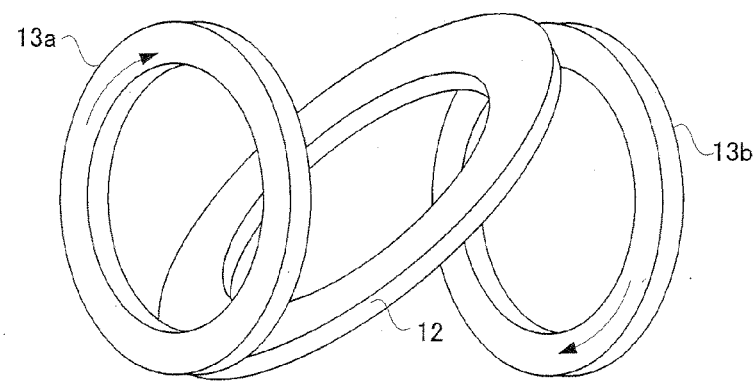
(b)
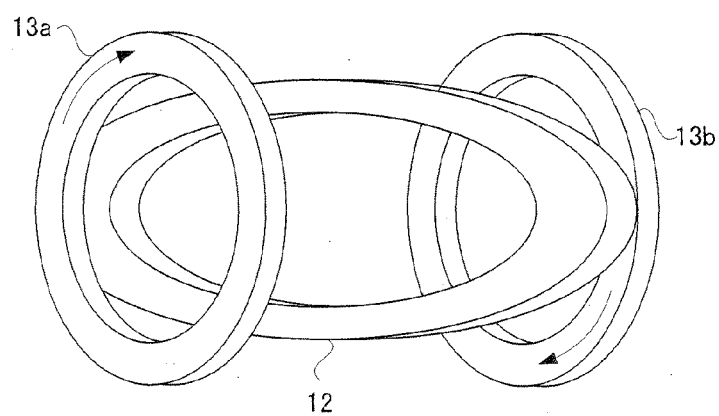
(c)
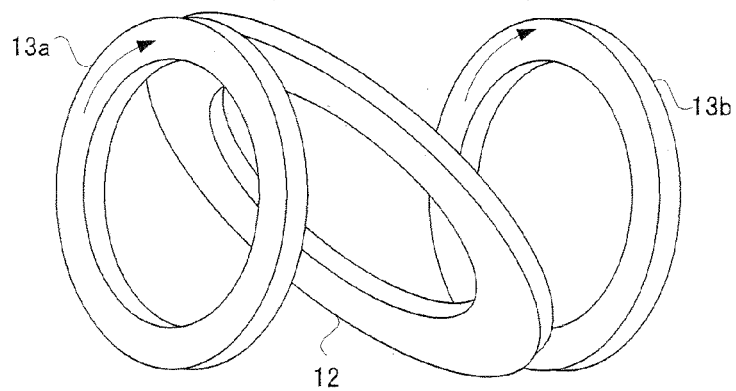

Fig.10
(a)
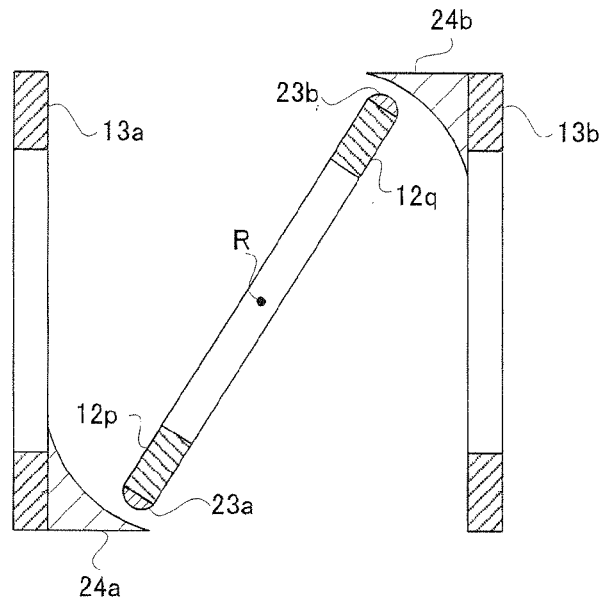
(b)
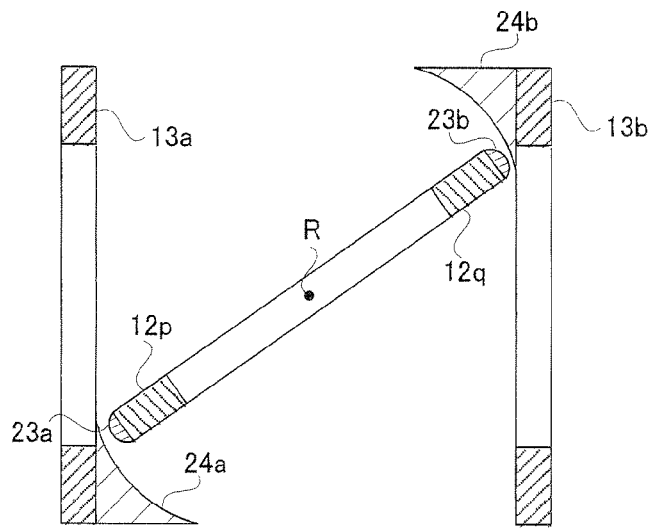

Fig.11
(a)
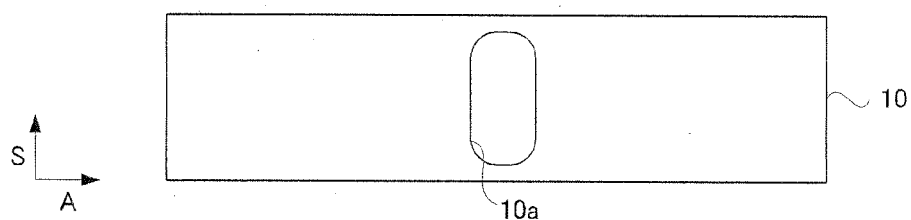
(b)
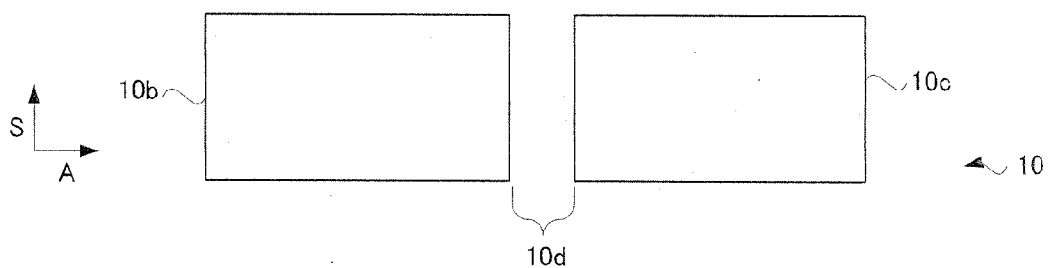
Fig.12
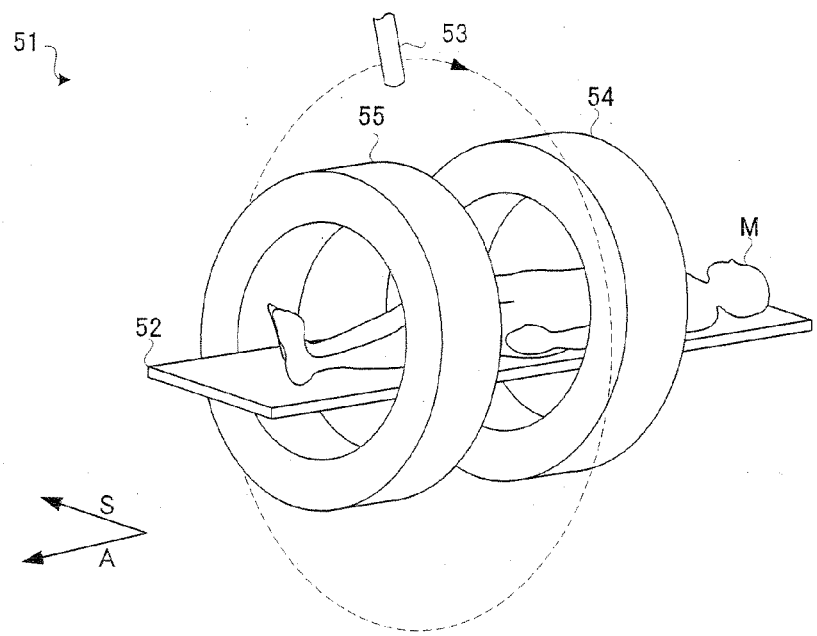

PARTICLE RADIOTHERAPY APPARATUS

TECHNICAL FIELD

This invention relates to a particle radiotherapy apparatus for carrying out medical treatment by emitting a particle beam to a patient, and more particularly relates to a particle radiotherapy apparatus which can monitor an irradiation area of a particle beam during medical treatment.

BACKGROUND ART

In treatment of cancer, for example, a lesion of a patient may be irradiated with radiation. In such radiotherapy, a particle radiotherapy apparatus which uses a particle beam has been developed (see Nonpatent Document 1, for example).

Such a particle radiotherapy apparatus will be described. As shown in FIG. 12, a conventional particle radiotherapy apparatus 51 includes a top board 52 for supporting a patient M, a particle beam source 53 for emitting a particle beam, and a first detector ring 54 and a second detector ring 55 for detecting annihilation gamma ray pairs generating from inside the patient M. The particle beam source 53 is disposed in a position between the two detector rings 54 and 55. And the particle beam source 53 can move around the patient M, about the body axis of the patient M. That is, a gap provided between the two detector rings 54 and 55 serves as a passage of the particle beam.

The construction of the two detector rings 54 and 55 will be described. The first detector ring 54 is constructed of blockish radiation detectors 61 arranged in a ring form. As shown in FIG. 13, this radiation detector 61 has a scintillator 62 for converting the radiation into fluorescence, and a photomultiplier tube (hereinafter called photodetector) 63 for detecting the fluorescence. The scintillator 62 has rectangular parallelepiped-shaped scintillator crystals C arranged in three dimensions. The photodetector 63 can determine which scintillator crystals C have emitted the fluorescence. That is, the radiation detector 61 can specify where on the scintillator 62 the radiation is incident. Of the surfaces of the scintillator 62, the surface remotest from the photodetector 63 will be called the plane of incidence 62a for expediency.

Next, a sectional view of the conventional particle radiotherapy apparatus 51 is shown. As shown in FIG. 14, the two detector rings 54 and 55 in the conventional particle radiotherapy apparatus 51 have the radiation detectors 61 arranged simply. That is, the scintillators 62 are directed inward of the two detector rings 54 and 55. Specifically, the scintillators 62 are directed to the same positions in the body axis direction A of the patient M.

When carrying out radiotherapy with the particle radiotherapy apparatus 51, a particle beam is emitted from the particle beam source 53 to the patient M placed on the top board 52. The particle beam source 53 moves around the body axis of the patient M while emitting the particle beam, and continues emitting the particle beam to the patient M while changing irradiation angle. The particle beam loses energy in the body of the patient M. At this time, the nucleus located at the point where the particle beam loses energy is converted into a nuclide which causes $\beta^+$ decay. This nucleus causes $\beta^+$ decay and emits a positron. The resulting positron encounters and annihilates with an electron present in the vicinity. At this time, a pair of annihilation gamma rays are produced, which move in 180° opposite directions. This annihilation gamma ray pair penetrate the patient M, and are detected by the two detector rings 54 and 55. The conventional particle radiotherapy apparatus 51 determines the location where this annihilation gamma ray pair have been produced, thereby to presume a point where the particle beam lost energy. Cells are destroyed adjacent the point where the particle beam lost energy. In this way, it can be found out whether the particle beam accurately aims at the lesion of the patient M. The annihilation gamma ray pairs are an example of radiation resulting from the particle beam.

In order to attain the object of determining the location where the annihilation gamma ray pair have been produced, both of the annihilation gamma ray pair must be detected. This is because the point of occurrence of the annihilation gamma ray pair is determined by obtaining a line (Line of Response: hereinafter referred to as LOR as appropriate) extending between two points where the annihilation gamma ray pair are detected.

[Nonpatent Document 1] "IEEE Nuclear Science Symposium Conference Record) (U.S.A), November 2007, No. 5, p 3688-3690

DISCLOSURE OF THE INVENTION

Problem to be Solved by the Invention

However, the conventional construction has the following drawback.

That is, according to the conventional construction, it is necessary to provide the passage for allowing movement of the particle beam source 53, which poses a problem that the sensitivity for detection of annihilation gamma ray pairs is not sufficient. That is, the sensitivity for detection of the annihilation gamma ray pairs falls victim to the restriction that the particle beam source 53 must always be in the same position as the position in the body axis direction A of the lesion of the patient M. Specifically, the sensitivity of the detector rings for detection of the annihilation gamma ray pairs depends greatly on the direction of incidence of the annihilation gamma ray pairs on the detector rings.

Supposing the positions of the first detector ring 54 and an annihilation point having produced an annihilation gamma ray pair are the same in the body axis direction A of the patient M, the annihilation gamma ray pair advance into the first detector ring 54 at substantially right angles to the body axis direction A. Then, as shown in FIG. 15 (a), one of the gamma rays forming the annihilation gamma ray pair is incident on the plane of incidence 62a of the scintillator 62, and moves toward the photodetector 63. Then, since the gamma ray passes through thick parts of the scintillator 62 in its movement toward the photodetector 63, the gamma ray is reliably converted into fluorescence, which constitutes high sensitivity for detecting the gamma ray.

On the other hand, the two detector rings 54 and 55 of the particle radiotherapy apparatus 51 are arranged clear of the passage through which the particle beam source 53 moves. Since the position in the body axis direction A of the lesion of the patient M and the particle beam source 53 must always be in the same position irrespective of revolution of the particle beam source 53, the point in the body axis direction A of the patient M at which the particle beam loses energy and the positions of the two detector rings 54 and 55 are different from each other. That is, an annihilation gamma ray pair advance into the first detector ring 54 from oblique directions with respect to the body axis direction A. Then, as shown in FIG. 15 (b), a gamma ray does not necessarily move from the plane of incidence 62a of the scintillator 62 toward the photodetector 63, but may move toward a side surface of the scintillator 62. Then, part of the gamma rays constituting annihilation gamma ray pairs bypass thick parts of the scintillators 62 and exit from side surfaces of the scintillators 62. Such gamma rays are never converted into fluorescence, and are not detected by the radiation detectors 61 after all.

That is, when an annihilation gamma ray pair advance into the first detector ring 54 from oblique directions with respect to the body axis direction A, the scintillators 62 have an insufficient thickness on paths of the gamma rays, at lateral ends in the body axis direction A. This is because the gamma rays incident on the planes of incidence 62a of the scintillators 62 bypass the central parts of the scintillators 62, and immediately move to side surfaces of the scintillators 62.

The gamma rays released from the patient M in the particle radiotherapy apparatus 51 are very small in quantity, compared with a PET (Positron Emission Tomography) apparatus which medicates a patient M with a radioactive substance which emits annihilation gamma ray pairs, and images a distribution of the latter, and its dose is about 1/1000 to 1/100 of the PET apparatus, for example.

That is, improving the sensitivity for detection of annihilation gamma ray pairs in the particle radiotherapy apparatus 51 leads to an accurate confirmation that the annihilation gamma ray pairs are produced in the lesion of the patient. This is a matter of great importance in developing the particle radiotherapy apparatus 51 which can carry out effective medical treatment.

The conventional construction includes the two detector rings 54 and 55. The two detector rings will increase the manufacturing cost of the particle radiotherapy apparatus 51. However, a single detector ring would be incapable of detecting both gamma rays of an annihilation gamma ray pair.

That is, in the particle radiotherapy apparatus 51, as shown in FIG. 16, a single detector ring may be sufficient as long as it can measure annihilation gamma rays advancing in a state of maintaining a position G in the body axis direction A of the patient M. However, the particle radiotherapy apparatus 51 is required to provide a passage for the particle beam, and therefore the radiation detector cannot be disposed in position G. That is, it is impossible to detect annihilation gamma rays advancing in the state of maintaining the position G. Instead, annihilation gamma ray pairs having directions of movement deviating from the above position G are detected. As shown in FIG. 16, one gamma ray of such an annihilation gamma ray pair advances forward in the body axis direction A of the patient M, while the other gamma ray advances backward in the body axis direction A of the patient M. It is impossible to detect such an annihilation gamma ray pair with a single detector ring. This is because the positions of the radiation detectors provided for the detector ring are the same positions with respect to the body axis direction A of the patient M. After all, the conventional construction cannot operate with a single detector ring.

This invention has been made having regard to the state of the art noted above, and its object is, in the particle radiotherapy apparatus which has a passage for allowing movement of a particle beam, to provide a particle radiotherapy apparatus with high sensitivity for detection of annihilation radiation pairs.

Means for Solving the Problem

To fulfill the above object, this invention provides the following construction.

A particle radiotherapy apparatus comprising a detector ring with an annular arrangement of radiation detectors that are formed by laminating, in one direction, a scintillator with a plane of incidence for receiving radiation and converting the radiation into fluorescence, a light guide for receiving and transmitting the fluorescence, and a photodetector for detecting the fluorescence, and comprises, in addition thereto, an elongated top board inserted in an opening of the detector ring, and a particle beam emitting device for emitting a particle beam, the particle radiotherapy apparatus further comprising a first ring having a central axis corresponding to a predetermined axis parallel to a direction of extension of the top board; a second ring having a central axis corresponding to the predetermined axis; a ring rotating device for rotating the first ring and the second ring about the predetermined axis; and a ring rotation control device for controlling the ring rotating device; wherein one end of the detector ring is supported by the first ring; the detector ring is tilted relative to the first ring, and extends from the one end toward the second ring, traversing the top board; the other end of the detector ring is supported by the second ring; and the detector ring makes rotating movement relative to the top board, in a state of being tilted relative to the first ring, with rotation of the first ring and the second ring.

[Functions and Effects] The particle radiotherapy apparatus according to this invention rotates the detector ring relative to the top board. Specifically, the detector ring is rotated by rotating the first ring and second ring supporting the detector ring. In addition, the detector ring is tilted relative to the first ring. That is, with rotation of the first ring and second ring, the detector ring will make rotating movement while being tilted relative to the first ring. Incidentally, the particle beam source emits a particle beam toward the top board. Therefore, the detector ring cannot be disposed in a position to interfere with travel of this particle beam. However, according to the construction of this invention, the detector ring is tilted relative to the top board, and besides makes rotating movement relative to the top board. This means also that the positional relationship between the detector ring and particle beam is changeable. Therefore, since the detector ring can be moved away from the particle beam by rotating the detector ring according to this invention, it is possible to provide the particle radiotherapy apparatus which can detect annihilation radiation while emitting the particle beam.

Moreover, annihilation radiation pairs are detected with the single detector ring. Then, the detector ring will detect annihilation radiation pairs occurring in its interior. In other words, all annihilation radiation pairs will impinge on the detector ring at substantially right angles. This inhibits the lowering of the sensitivity for detection described using FIG. 15.

It is preferred that the detector ring has an elliptic shape with a long axis consisting of a line segment extending between the one end and the other end thereof.

[Functions and Effects] According to the above construction, the particle radiotherapy apparatus is provided which can introduce a patient with increased reliability. That is, the patient is introduced into the tilted detector ring. If the detector ring has an elliptic shape at this time, it is possible to prevent the detector ring and top board from approaching each other due to tilting of the detector ring relative to the top board. In other words, the detector ring according to the above construction can be given an elliptical shape extending to both sides to avoid interference with the top board.

It is preferred that the above detector ring is arranged to detect radiation resulting from the particle beam, after being rotated by the ring rotating device and in a state of its rotating angle being maintained.

[Functions and Effects] According to the above construction, the particle radiotherapy apparatus provided has high sensitivity for detecting annihilation radiation. It is predicted that various nuclides are generated at points inside the body of the patient where the particle beam lost energy. The energies and characteristics of the radiation released by decay thereof are varied. It is possible that single photons which are not annihilation gamma ray pairs are released. Such single photons may be detected by the detector ring. These cause noise when imaging positions of action of the particle beam using the annihilation gamma ray pairs. However, according to the above construction, the rotating angle of the detector ring can be optimized. Specifically, the particle beam may be emitted in a state of a desired rotating angle of the detector ring being maintained.

It is preferred to comprise a first shifting device disposed in a position between the above one end of the detector ring and the first ring, for moving the one end forward and backward relative to the second ring and along an arcuate locus; a first shift control device for controlling this; a second shifting device disposed in a position between the other end of the detector ring and the second ring, for moving the other end forward and backward relative to the first ring and along an arcuate locus; and a second shift control device for controlling this; wherein the first shifting device and the second shifting device are arranged to tilt the detector ring relative to the first ring about a middle point of a line segment extending between the one end and the other end.

[Functions and Effects] According to the above construction, the particle radiotherapy apparatus provided has a still higher sensitivity for detecting annihilation radiation. It is desirable to render the positional relationship between the top board and detector ring freely changeable in order to remove the influence of noise as much as possible when imaging an action position of a particle beam using annihilation gamma ray pairs. According to the above construction, not only the rotating angle relative to the top board of the detector ring, but the tilt angle relative to the top board of the detector ring can be changed. For example, when the one end is moved toward the second ring, the other end is moved toward the first ring. When the one end is moved away from the second ring, the other end is moved away from the first ring. This provides an increased degree of freedom for changing the positional relationship between the top board and detector ring, thereby realizing high sensitivity for detecting annihilation radiation.

The detector ring may be arranged to detect radiation resulting from the particle beam while being tilted by the first shifting device and the second shifting device.

The detector ring may be arranged to detect radiation resulting from the particle beam, after being tilted by the first shifting device and the second shifting device and in a state of its tilt angle being maintained.

[Functions and Effects] According to the above construction, tilting of the detector ring, including also its direction, can be optimized. Specifically, it may be constructed to emit particle beams while tilting the detector ring, in order to determine a positional relationship between the top board and elliptic detector ring producing little noise and well suited for imaging. When a desired tilt of the detector ring is known, particle beams may be emitted in a state of the tilt angle being maintained.

Effects of the Invention

The particle radiotherapy apparatus according to this invention rotates the detector ring relative to the top board. Specifically, with rotation about a predetermined axis of the first ring and second ring, the detector ring will make rotating movement while being tilted relative to the first ring. Incidentally, the particle beam source emits a particle beam toward the top board. Therefore, the detector ring cannot be disposed in a position to interfere with travel of this particle beam. According to the construction of this invention, the detector ring is tilted relative to the top board, and besides makes rotating movement relative to the top board. This means also that the positional relationship between the detector ring and particle beam is changeable. Therefore, since the detector ring can be moved away from the particle beam by rotating the detector ring according to this invention, it is possible to provide the particle radiotherapy apparatus which can detect annihilation radiation while emitting the particle beam.

BRIEF DESCRIPTION OF THE DRAWINGS

FIG. 6 is a schematic view illustrating rotating movement of the elliptic detector ring according to Embodiment 1;

FIG. 10 is a sectional view illustrating tilting movement of an elliptic detector ring according to Embodiment 2;

FIG. 11 is a perspective view illustrating a construction of a top board according to one modification of this invention;

FIG. 12 is a perspective view illustrating a construction of a conventional particle radiotherapy apparatus;

Figure 1:
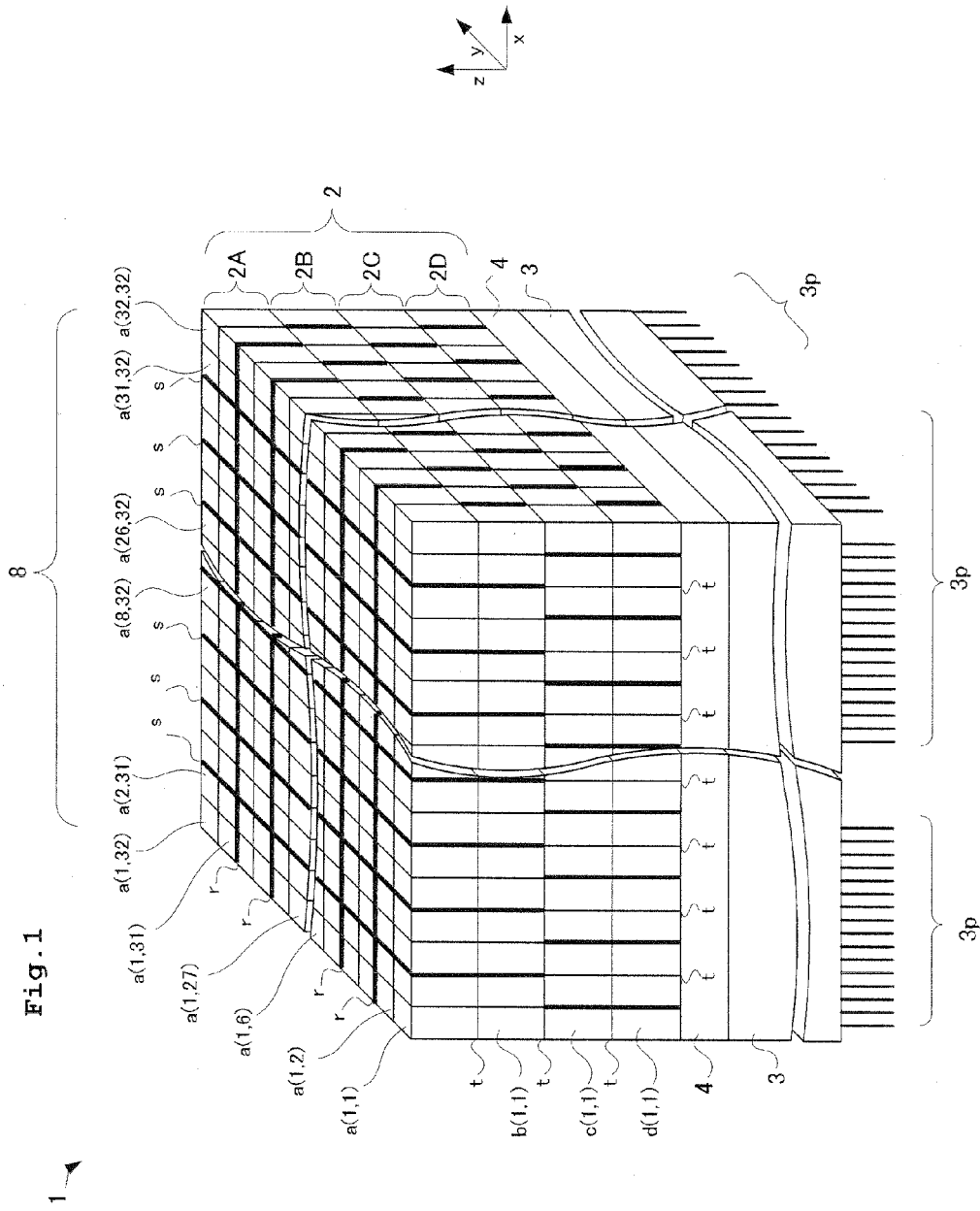
FIG. 1 is a perspective view of a radiation detector according to Embodiment 1.

DESCRIPTION OF REFERENCES 1 radiation detector
2 scintillator
3 photodetector
4 light guide
10 top board
12 elliptic detector ring (detector ring)
12$p$ one end
12$q$ other end
13$a$ first ring
13$b$ second ring
25$a$ first shift mechanism (first shifting device)
25$b$ second shift mechanism (second shifting device)
31 particle beam source (particle beam emitting device)
32 ring rotating mechanism (ring rotating device)
33 ring rotation control unit (ring rotation control device)

BEST MODE FOR CARRYING OUT THE INVENTION

The best mode of particle radiotherapy apparatus according to this invention will be described hereinafter with reference to the drawings. Gamma rays in the following description are one example of radiation in this invention.

Embodiment 1

First, a construction of a radiation detector 1 according to Embodiment 1 will be described in advance of description of a particle radiotherapy apparatus according to Embodiment 1. FIG. 1 is a perspective view of a radiation detector according to Embodiment 1. As shown in FIG. 1, the radiation detector 1 according to Embodiment 1 includes a scintillator 2 formed of each of scintillator crystal layers laminated in z-direction in order of scintillator crystal layer 2D, scintillator crystal layer 2C, scintillator crystal layer 2B and scintillator crystal layer 2A, a photomultiplier tube (hereinafter called photodetector) 3 disposed on a lower surface of the scintillator 2 and having a position specifying function for detecting fluorescence emitted from the scintillator 2, and a light guide 4 disposed in a position interposed between the scintillator 2 and photodetector 3 for receiving and transmitting the fluorescence. Therefore, each of the scintillator crystal layers is laminated in a direction toward the photodetector 3. The scintillator crystal layer 2A serves as a plane of incidence 8 of radiation on the scintillator 2. In other words, the surface opposed to the photodetector 3 among the surfaces of the scintillator 2 is the plane of incidence. Each of the scintillator crystal layers 2A, 2B, 2C and 2D is optically coupled, and transmission members t are formed between the respective layers. As a material for these transmission members t, a thermosetting resin such as silicon resin may be used. The scintillator crystal layer 2A serves as a light receiver of gamma rays emitted from a radiation source, and is formed of blockish scintillator crystals arranged in a two-dimensional matrix form having 32 crystals in x-direction and 32 crystals in y-direction with scintillator crystal a(1, 1) acting as the basis. That is, scintillator crystal a(1, 1)—scintillator crystal a(1, 32) are arranged in y-direction to form a scintillator crystal array. The scintillator crystal layer 2A is formed of 32 such scintillator crystal arrays arranged in x-direction. The scintillator crystal layers 2B, 2C and 2D also are formed of scintillator crystals arranged in a two-dimensional matrix form having 32 crystals in x-direction and 32 crystals in y-direction with scintillator crystals b(1, 1), c(1, 1) and d(1, 1) acting as the bases, respectively. In each of the scintillator crystal layers 2A, 2B, 2C and 2D, transmission members t are formed also between adjacent scintillator crystals. Therefore, each of the scintillator crystals is surrounded by the transmission members t. The thickness of these transmission members t is about 25 μm. The gamma rays correspond to the radiation in this invention.

The scintillator crystal layers 2A, 2B, 2C and 2D provided for the scintillator 2 have first reflectors r extending in x-direction and second reflectors s extending in y-direction. Both these reflectors r and s are inserted in gaps between the scintillator crystals arranged.

The scintillator 2 is constructed of scintillator crystals suitable for detection of gamma rays and arranged in three dimensions. That is, the scintillator crystals are formed of $Lu_{2(1-X)}Y_{2X}SiO_5$ (hereinafter called LYSO) diffused with Ce. Each of the scintillator crystals, irrespective of the scintillator crystal layers, is a rectangular parallelepiped which is, for example, 1.45 mm long in x-direction, 1.45 mm wide in y-direction, and 4.5 mm high in z-direction. Of the surfaces of the scintillator 2, the four side surfaces continuous with the light guide 4 are covered with reflective film not shown. The photodetector 3 is the multi-anode type, which can determine positions relating to x and y of incident fluorescence.

The light guide 4 is provided in order to guide the fluorescence generated in the scintillator 2 to the photodetector 3. Therefore, the light guide 4 is optically coupled to the scintillator 2 and photodetector 3. A plurality of connecting terminals 3p are provided on a bottom surface of the photodetector 3 remote from the scintillator 2. These connecting terminals 3p are connected to a bleeder unit 21 to be described hereinafter.

Figure 2:
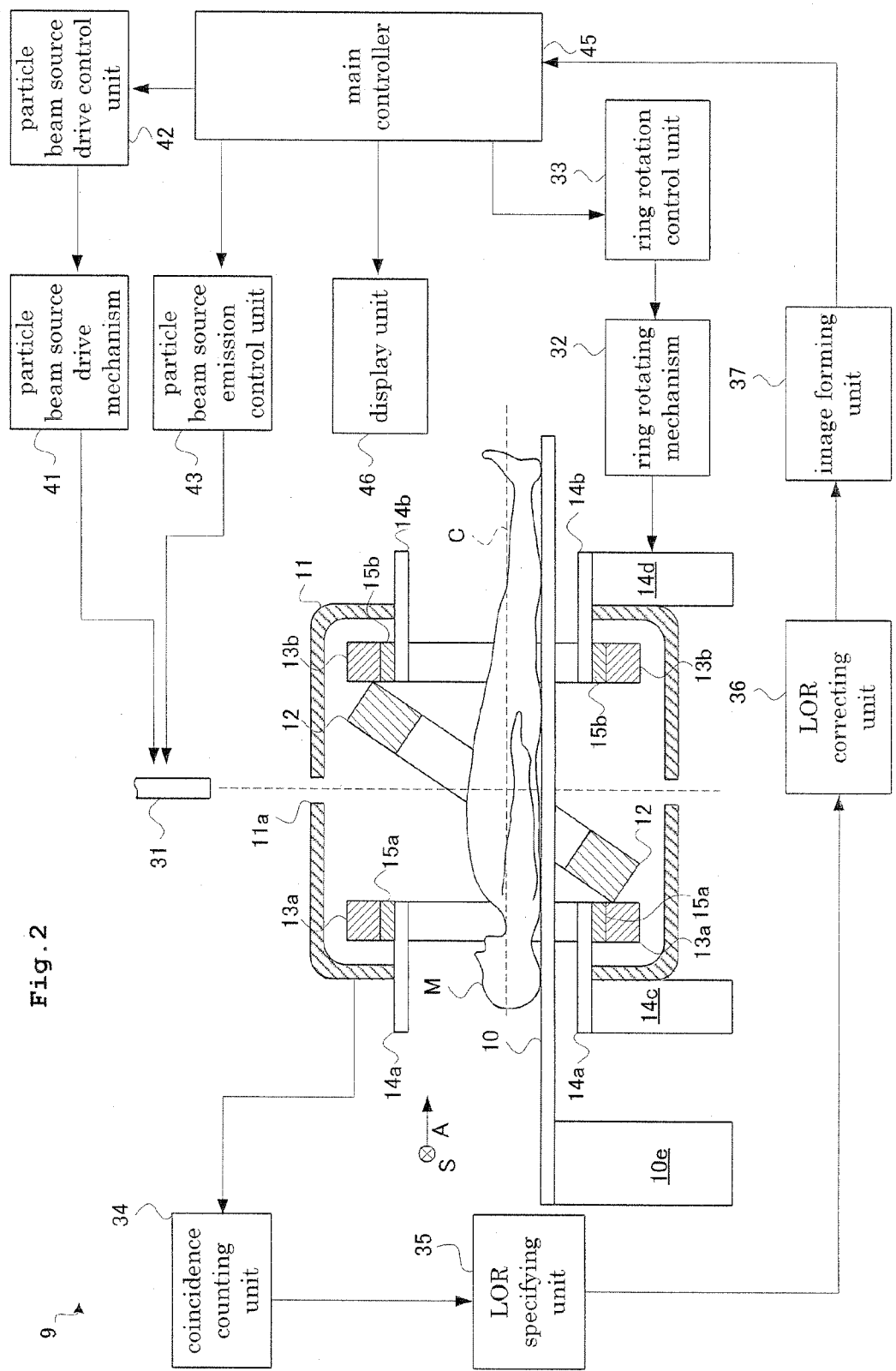
FIG. 2 is a functional block diagram illustrating a construction of a particle radiotherapy apparatus according to Embodiment 1.

Next, a particle radiotherapy apparatus 9 according to Embodiment 1 will be described. FIG. 2 is a functional block diagram illustrating a construction of a particle radiotherapy apparatus according to Embodiment 1. As shown in FIG. 2, the particle radiotherapy apparatus 9 according to Embodiment 1 includes a top board 10 for supporting a patient M, a gantry 11, and an elliptic detector ring 12 mounted inside the gantry 11. The elliptic detector ring 12 corresponds to the detector ring in this invention. The top board 10 is slidably supported by a support deck 10e installed on a floor.

The gantry 11 has an annular slit 11a formed therein to divide the gantry 11 in order to secure a passage for a particle beam. This slit 11a is provided to introduce a particle beam emitted from a particle beam source 31 to be described hereinafter, into the interior of the gantry 11.

A first ring 13a and a second ring 13b are mounted inside the gantry 11. The first ring 13a has a central axis thereof coinciding with a base axis C parallel to a direction of extension of the top board (body axis direction A of the patient M). Similarly, the second ring 13b also has a central axis thereof coinciding with the base axis C. The elliptic detector ring 12 is mounted between and supported by these first ring 13a and second ring 13b. Specifically, one end of the elliptic detector ring 12a is supported by the first ring 13a, while the other end of the elliptic detector ring 12 is supported by the second ring 13b. Moreover, the elliptic detector ring 12 is tilted relative to the first ring 13a and second ring 13b. The lower end of the first ring 13a and the lower end of the elliptic detector ring 12 are coupled together. The upper end of the second ring 13b and the upper end of the elliptic detector ring 12 are coupled together. In this way, the elliptic detector ring 12 is tilted relative to the two rings 13a and 13b. In other words, the elliptic detector ring 12 is disposed to bridge the lower end of the first ring 13a and the upper end of the second ring 13b, once traversing the top board 10. The base axis corresponds to the predetermined axis in this invention.

The particle radiotherapy apparatus 9 includes a ring rotating mechanism 32 for rotating the first ring 13a and second ring 13b, and a ring rotation control unit 33 for controlling this. The ring rotating mechanism 32 rotates the first ring 13a and second ring 13b in the same direction and at the same speed about the base axis C. This causes the elliptic detector ring 12 to make rotating movement in the state of being tilted relative to the two rings 13a and 13b. The elliptic detector ring 12 makes the rotating movement about the base axis C circumferentially of the top board 10. The ring rotating mechanism and ring rotation control unit correspond to the ring rotating device and ring rotation control device in this invention, respectively.

The first ring 13a has a first bearing 15a mounted on the inner side thereof for making the first ring 13a movable. And the first bearing 15a has an annular, first support tube 14a mounted on the inner side thereof for supporting the first bearing 15a, which is fixed to the floor by a tube anchor 14c.

Similarly, the second ring 13b has a second bearing 15b mounted on the inner side thereof for making the second ring 13b movable. And the second bearing 15b has an annular, second support tube 14b mounted on the inner side thereof for supporting the second bearing 15b, which is fixed to the floor by a tube anchor 14d.

The particle radiotherapy apparatus 9 further includes various components to acquire sectional images of the patient M. Specifically, the particle radiotherapy apparatus 9 includes a coincidence counting unit 34 for receiving gamma ray detection signals from the elliptic detector ring 12, which signals indicate detected positions, detected strengths and detected times of gamma rays, and carrying out coincidence counting of annihilation gamma ray pairs, an LOR specifying unit 35 for specifying an LOR, to be described hereinafter, from two gamma ray detection data determined to be an annihilation gamma ray pair by the coincidence counting unit 34, an LOR correcting unit 36 for correcting the LOR, and an image forming unit 37 for forming radiation sectional images of a site of interest.

The particle radiotherapy apparatus 9 according to Embodiment 1 has a particle beam source 31 for emitting a particle beam. The particles emitted from the particle beam source 31 are protons or carbon nuclei, for example, but are not limited to these. This particle beam source 31 is driven by a particle beam source drive mechanism 41, and is capable of revolving movement about the base axis C extending along the body axis direction A of the patient M. This particle beam source drive mechanism 41 is controlled by a particle beam source drive control unit 42. Emission of particles from the particle beam source 31 is controlled by a particle beam source emission control unit 43. The particle beam source 31 is revolved about the body axis of the patient M while the direction of particle emission from the particle beam source 31 is changed. Specifically, the particle beam source 31 emits a particle beam in a direction toward the base axis C irrespective of the revolving movement. That is, the particle beam source 31 will emit the particle beam toward one point belonging to the base axis C irrespective of the revolving movement. The particle beam emitted from the particle beam source 31 is introduced into the interior of the gantry 11 by passing through the above-mentioned slit 11a. The particle beam source corresponds to the particle beam emitting device in this invention.

The particle radiotherapy apparatus 9 according to Embodiment 1 further includes a main controller 45 for carrying out overall control of the various control units, and a display unit 46 for displaying radiation sectional images. This main controller 45 is formed of a CPU, which executes various programs to realize the coincidence counting unit 34, LOR specifying unit 35, LOR correcting unit 36, image forming unit 37, particle beam source drive control unit 42 and particle beam source emission control unit 43.

Figure 3:
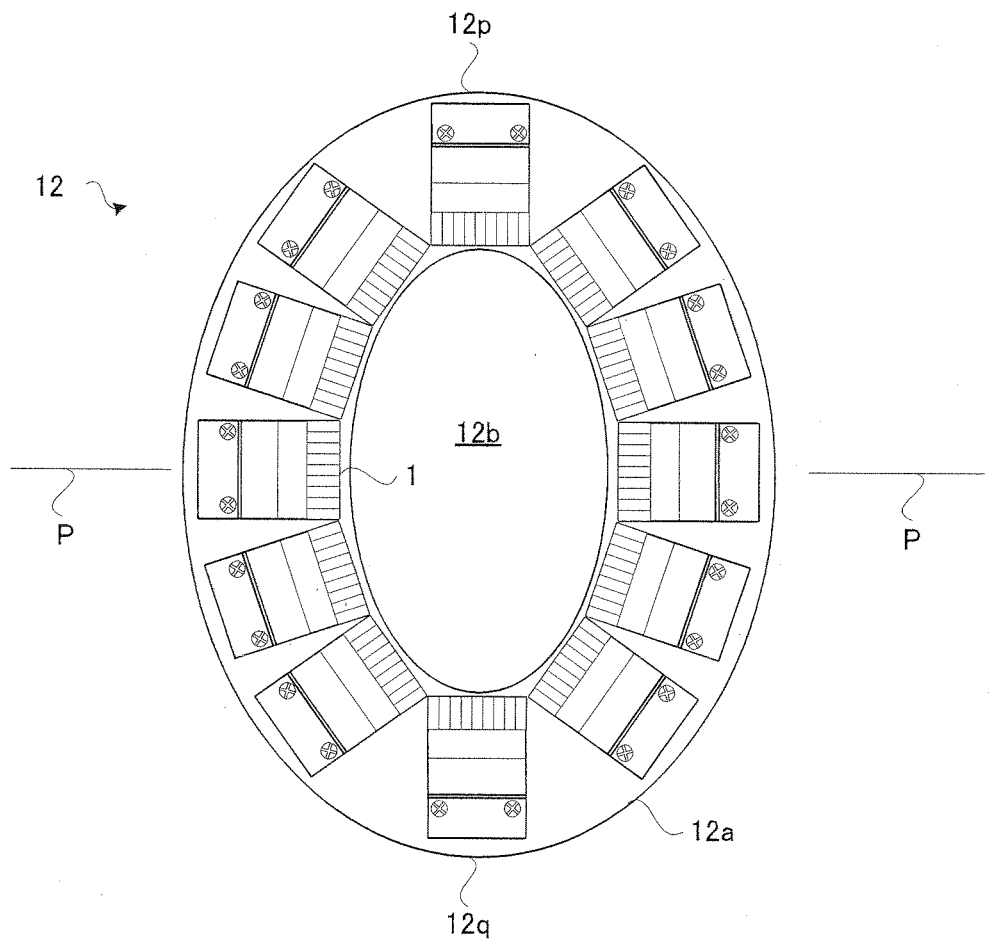
FIG. 3 is a plan view illustrating a construction of an elliptic detector ring according to Embodiment 1.

Next, the construction of the elliptic detector ring 12 according to Embodiment 1 will be described. As shown in FIG. 3, the elliptic detector ring 12 has an elliptic type elliptic plate 12a with an elliptic type opening 12b formed centrally thereof. Radiation detectors 1 are annularly arranged along this elliptic plate 12a to form the elliptic detector ring 12. Therefore, the elliptic detector ring 12 has an elliptic opening 12b at the center. The radiation detectors 1 have the planes of incidence all arranged to face the opening 12b of the elliptic detector ring 12. The elliptic detector ring 12 has an elliptic shape which is vertically long. P in the drawing indicates the short axis of the elliptic detector ring 12 having the elliptic shape. The opposite ends with respect to the long axis of the elliptic detector ring 12 are defined as one end 12p and the other end 12q.

Figure 4:
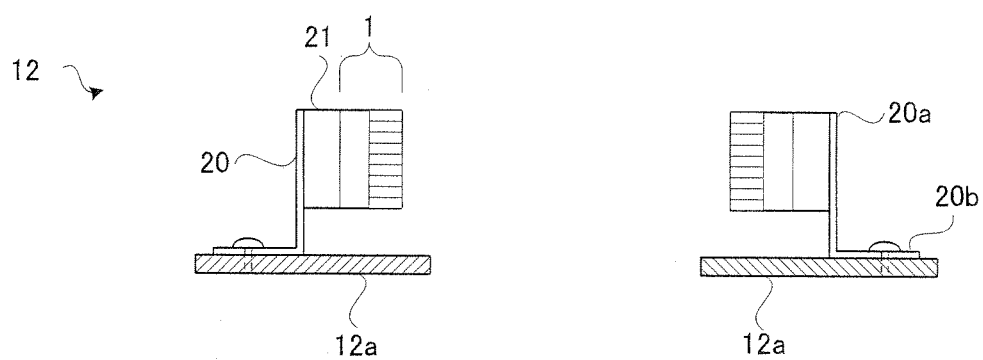
FIG. 4 is a sectional view illustrating the construction of the elliptic detector ring according to Embodiment 1.

FIG. 4 is a sectional view of the elliptic detector ring 12 according to Embodiment 1. This sectional view is a sectional view of the elliptic detector ring 12 cut along the direction of extension of the opening thereof. As shown in FIG. 4, the radiation detectors 1 are provided with bleeder units 21 for supplying electric power thereto. A first radiation detector and bleeder unit 21 are rigidly held together by an L-shaped holder 20. The holder 20 has a main plate 20a for fixing the bleeder unit 21, and an auxiliary plate 20b for fixing the holder 20 itself to the elliptic plate 12a. The bleeder unit 21 is fixed to the elliptic plate 12a through the holder 20.

Figure 5:
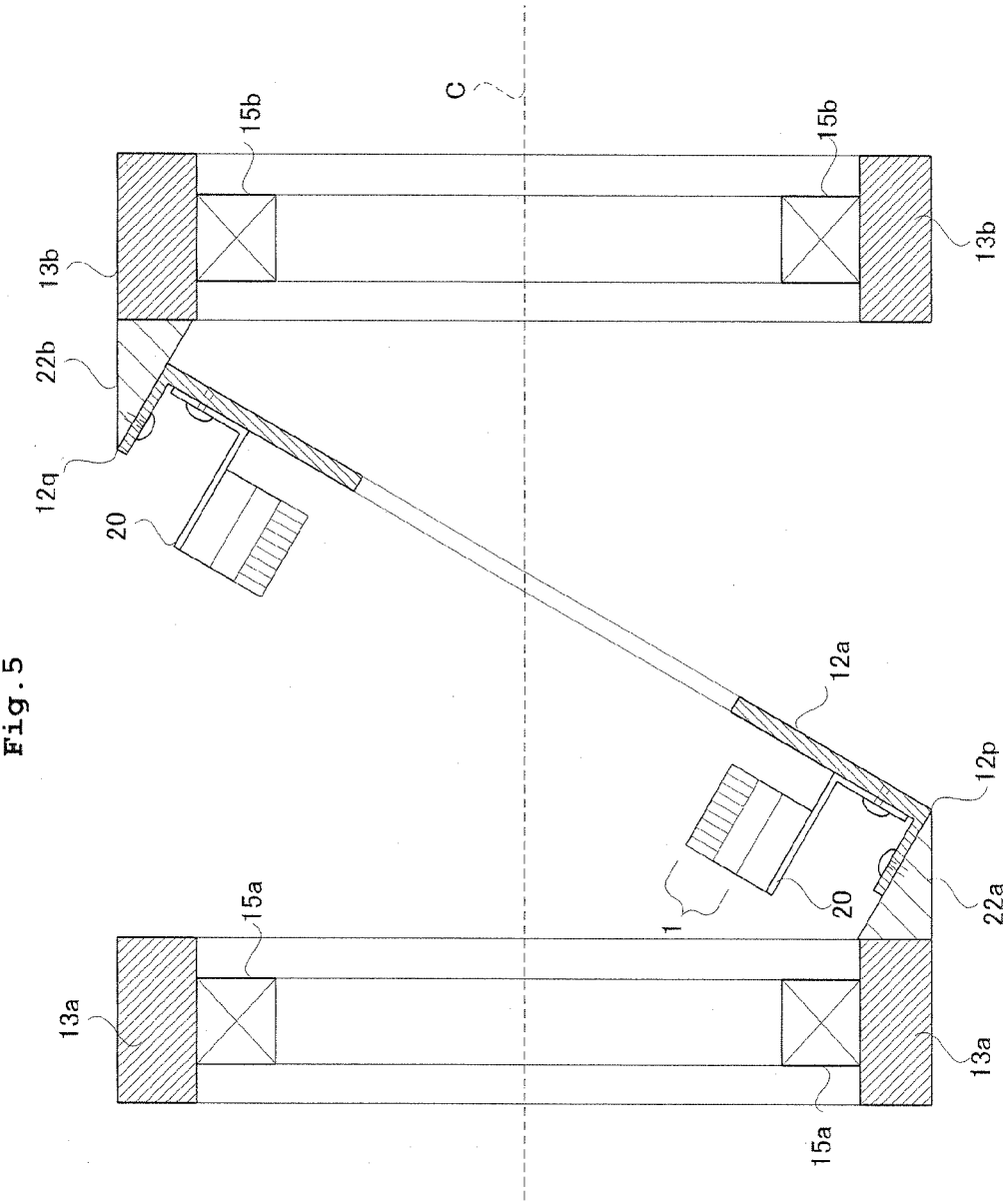
FIG. 5 is a sectional view illustrating the construction of the elliptic detector ring according to Embodiment 1.

Next, a relationship between the elliptic detector ring 12, first ring 13a and second ring 13b will be described. FIG. 5 is a sectional view illustrating a construction of the elliptic detector ring according to Embodiment 1. As shown in FIG. 5, the elliptic detector ring 12 has a projection projecting in L-shape from a side surface at one end 12p thereof, and the projection is fixed to a first coupling member 22a. And the first coupling member 22a is fixed to the first ring 13a. Similarly, the elliptic detector ring 12 has a projection projecting in L-shape from a side surface at the other end 12q thereof, and the projection is fixed to a second coupling member 22b. And the second coupling member 22b is fixed to the second ring 13b.

Next, rotating movement of the elliptic detector ring 12 will be described. Under control of the ring rotation control unit 33, the elliptic detector ring 12 can rotate clockwise, and can also rotate counterclockwise. FIG. 6 (a) shows an initial state in which the elliptic detector ring 12 has not made a rotating movement. This state of the elliptic detector ring 12 represents the state in FIG. 1. When, from this state, the first ring 13a and second ring 13b are rotated in the direction indicated by arrows, the elliptic detector ring 12 assumes a state as shown in FIG. 6 (b). When, from this state, the first ring 13a and second ring 13b are further rotated in the direction indicated by arrows, the elliptic detector ring 12 assumes a state as shown in FIG. 6 (c). The patient M is placed inwardly of this elliptic detector ring 12, and is irradiated with particle beams.

It is predicted that various nuclides are generated at points inside the body of the patient M where the particle beam lost energy. The energies and characteristics of the radiation released by decay thereof are varied. It is possible that single photons which are not annihilation gamma ray pairs are released. Such single photons may be detected by the elliptic detector ring 12. Such single photons cause noise when mapping positions of action of the particle beam using the annihilation gamma ray pairs. However, since the elliptic detector ring 12 can make rotating movements freely according to the construction in Embodiment 1, the tilt angle of the elliptic detector ring 12 can be varied to realize an optimal S/N ratio according to the type of medical treatment. For example, the tilt shown in FIG. 6 (b) can provide a better S/N ratio than the tilt shown in FIG. 6 (a).

Furthermore, regarding rotational positions of the elliptic detector ring 12, it can be better if the elliptic detector ring 12 is present between the particle beam source 31 and the patient M. In FIG. 6 (b), when the particle beam source 31 is located in a vertically upward position, a particle beam will collide with the elliptic detector ring 12, and will not reach the patient. However, even if the rotational position of the elliptic detector ring 12 is as in FIG. 6 (b), an annihilation gamma ray pair can be detected. That is, before emitting a particle beam from the particle beam source 31, the elliptic detector ring 12 may be rotated from the state of FIG. 6 (b). A particle beam may be emitted in this state, and after stopping emission of the particle beam, the elliptic detector ring 12 may be returned to the state of FIG. 6 (b). Consequently, an annihilation gamma ray pair can be detected, while emitting a particle beam to the patient M. A nuclide which releases annihilation gamma rays is generated at a point where the particle beam lost energy. However, this does not necessarily emit an annihilation gamma ray pair immediately. Therefore, while the nuclide which releases an annihilation gamma ray pair is still alive, the elliptic detector ring 12 is returned to the position of the initial state, and detection of the annihilation gamma ray pair is started. Then, the annihilation gamma ray pair may be detected in a state of good S/N ratio.

Figure 7:
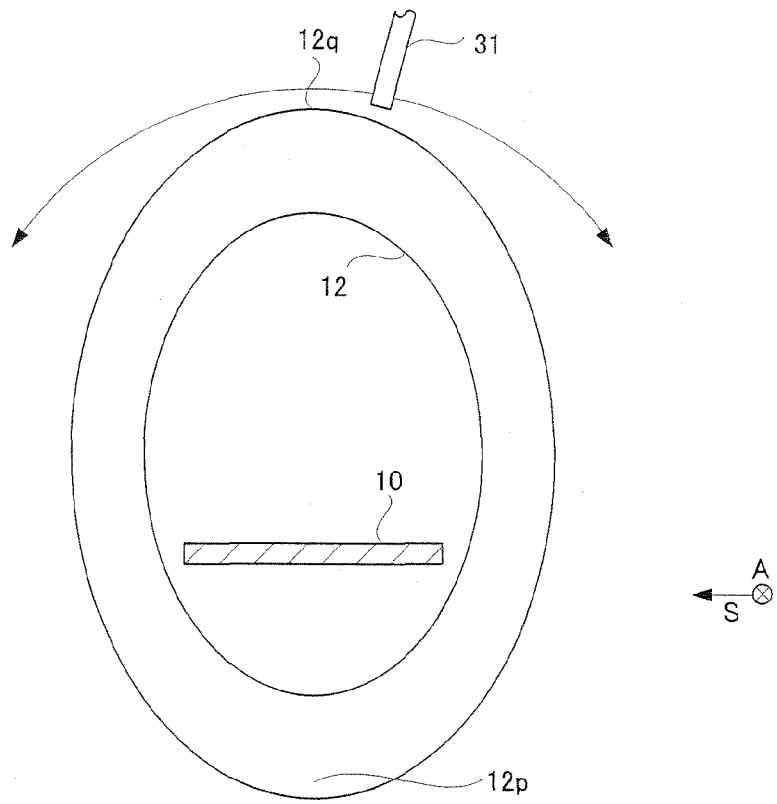
FIG. 7 is a sectional view illustrating revolution of a particle beam source according to Embodiment 1.

Next, revolving movement of the particle beam source 31 will be described. FIG. 7 is a sectional view illustrating revolution of the particle beam source according to Embodiment 1. As shown in FIG. 7, the particle beam source 31 can make revolving movement about the body axis of the patient M by revolving from a position vertically upward of the elliptic detector ring 12. The particle beam source 31 can make a circle about the body axis of the patient M. However, a particle beam is not always emitted during the revolving movement. When the particle beam source 31 is in the position where a particle beam collides with the elliptic detector ring 12, the emission of a particle beam is stopped.

Figure 8:
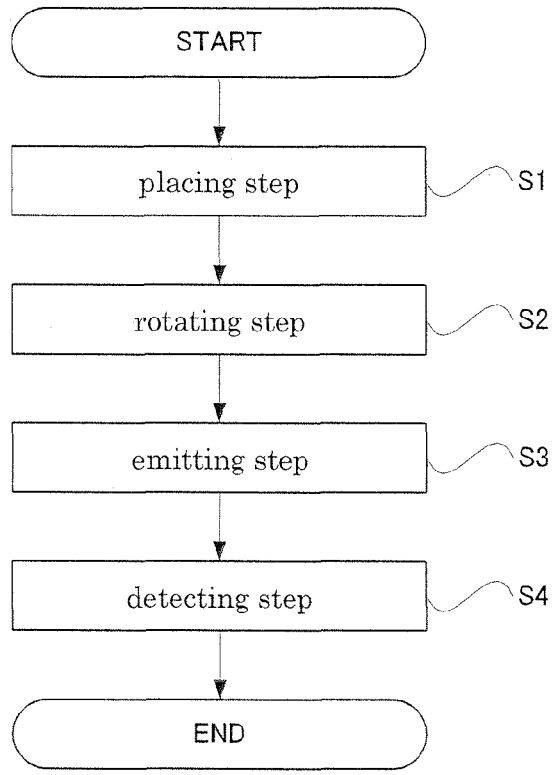
FIG. 8 is a flow chart illustrating operation of the particle radiotherapy apparatus according to Embodiment 1.

Next, operation of the particle radiotherapy apparatus 9 having such construction will be described. As shown in FIG. 8, operation of the particle radiotherapy apparatus 9 includes a placing step S1 for placing the patient M on the top board 10, a rotating step S2 for rotating the elliptic detector ring 12, an emitting step S3 for emitting a particle beam from the particle beam source 31 toward the patient M, and a detecting step S4 for detecting annihilation gamma rays generating from the particle beam. Particulars of each of these steps will be described in order hereinafter.

First, the patient M is placed on the top board 10 (placing step S1). Then, the operator causes movement of the top board 10 along the body axis direction A of the patient M to set the lesion of the patient M to a position in the passage of the particle beam emitted from the particle beam source 31. Next, the operator gives instructions for the elliptic detector ring 12, whereupon the elliptic detector ring 12 is rotated to a rotating angle and in a rotational direction as instructed by the operator (rotating step S2). The particle radiotherapy apparatus 9, with the elliptic detector ring 12 set to a predetermined tilt angle, is permitted to emit the particle beam, and stands by until the operator gives instructions. When the operator instructs emission of the particle beam, the particle beam is emitted from the particle beam source 31 (emitting step S3). Then, annihilation gamma ray pairs generating from the particle beam are detected by the elliptic detector ring 12 (detecting step S4). The image forming unit 37 creates a distribution map of the annihilation gamma rays detected from the patient M based on detection data outputted from the elliptic detector ring 12. This is displayed on the display unit 46, which enables the operator to check whether the particle beam reaches the lesion properly. In this way, the operation of the particle radiotherapy apparatus 9 according to Embodiment 1 is completed. The above tilting step S2 and emitting step S3 may be executed at the same time. That is, the particle beam may be emitted while the elliptic detector ring 12 is in rotating movement.

Next, data processing of the particle radiotherapy apparatus 9 according to Embodiment 1 will be described referring to FIG. 2. An annihilation gamma ray pair produced inside the patient M will be detected by certain of the radiation detectors 1 provided for the elliptic detector ring 12. The elliptic detector ring 12 outputs detection data resulting from detection of gamma rays to the coincidence counting unit 34. When detection data derived from two different scintillator crystals is included in a time window having a predetermined duration, the coincidence counting unit 34 regards this as being due to an annihilation gamma ray pair, and counts the number of times thereof. This is a count number.

The LOR specifying unit 35 deduces the exiting directions of the annihilation gamma ray pair. That is, the detection data regarded as coincident by the coincidence counting unit 34 includes positional information indicating which scintillator crystals emitted fluorescence. The LOR specifying unit 35 deduces an LOR (Line of Response) which is a line segment linking these two scintillator crystals, and outputs the LOR and a count number corresponding thereto to the LOR correcting unit 36.

As a characteristic arrangement of the construction in Embodiment 1, it is noted that the detection data outputted from the elliptic detector ring 12 includes information on the rotational direction and rotating angle of the elliptic detector ring 12. The LOR correcting unit 36 makes a correction of the LOR to remove the influence of rotation of the elliptic detector ring 12. According to the construction in Embodiment 1, rotation of the elliptic detector ring 12 will change a relative positional relationship between the elliptic detector ring 12 and the patient M. Besides, the LOR shows only a relative position in the elliptic detector ring 12 of a position of occurrence of the annihilation gamma ray pair. With such construction, since the directions indicated by the LOR changes with the rotating angle of the elliptic detector ring 12, it is impossible, after all, to determine where the annihilation gamma rays have occurred. However, according to the construction in Embodiment 1, a correction is made to incline the LOR virtually based on the information on the rotational direction and rotating angle of the elliptic detector ring 12, which information is included in the detection data. Thus, the influence of changes in the rotation of the elliptic detector ring 12 has been removed from data outputted from the LOR correcting unit 36. Therefore, the construction in Embodiment 1 can determine the position of occurrence of the annihilation gamma ray pair even if the elliptic detector ring 12 is rotated. This corrected LOR and a count number corresponding thereto are outputted to the image forming unit 37.

Based on corrected LORs and count numbers corresponding thereto, the image forming unit 37 maps an occurrence distribution of annihilation gamma ray pairs in a sectional plane of the patient M. A sectional image formed in this way is displayed on the display unit 46. The occurrence distribution of annihilation gamma ray pairs displayed enables monitoring of the site where the particle beam lost energy in the sectional plane of the patient M. In this way, it can be checked whether the particle beam in the particle radiotherapy apparatus 9 reliably acts on the lesion of the patient M.

As described above, the particle radiotherapy apparatus 9 according to Embodiment 1 rotates the elliptic detector ring 12 relative to the top board 10. Specifically, the elliptic detector ring 12 is rotated by rotating the first ring 13a and second ring 13b supporting the elliptic detector ring 12. In addition, the elliptic detector ring 12 is tilted relative to the first ring 13a. That is, with rotation of the first ring 13a and second ring 13b, the elliptic detector ring 12 will make rotating movement while being tilted relative to the first ring 13a. Incidentally, the particle beam source 31 emits a particle beam toward the top board 10. Therefore, the elliptic detector ring 12 cannot be disposed in a position to interfere with travel of this particle beam. According to the construction in Embodiment 1, the elliptic detector ring 12 is tilted relative to the top board 10, and besides makes rotating movement relative to the top board 10. This means also that the positional relationship between the elliptic detector ring 12 and particle beam is changeable. Therefore, since the elliptic detector ring 12 can be moved away from the particle beam by rotating the elliptic detector ring 12 according to Embodiment 1, it is possible to provide the particle radiotherapy apparatus 9 which can detect annihilation gamma rays while emitting the particle beam.

Figure 15:
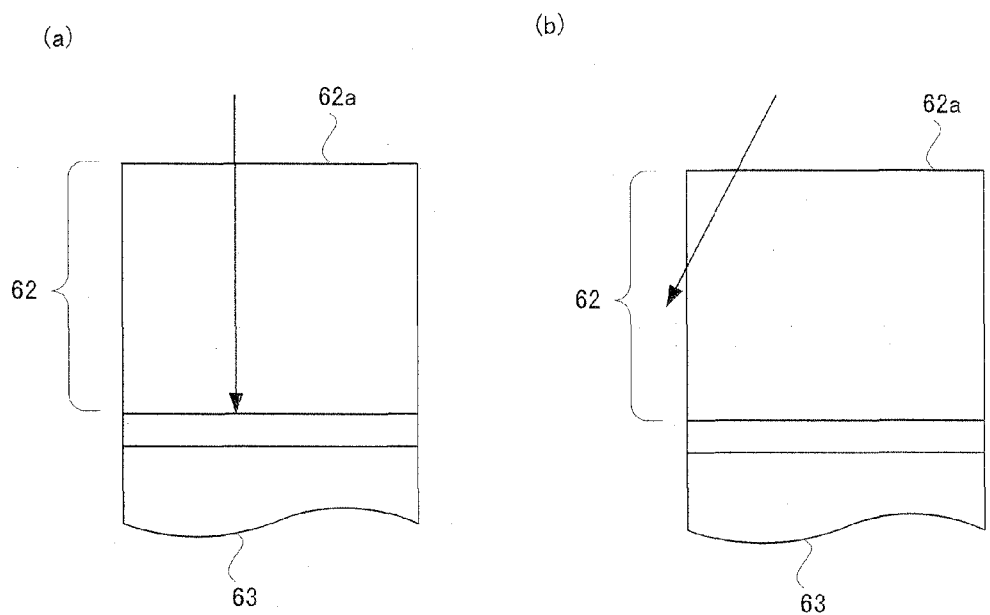
FIG. 15 is a sectional view illustrating the construction of the conventional particle radiotherapy apparatus.
Figure 16:
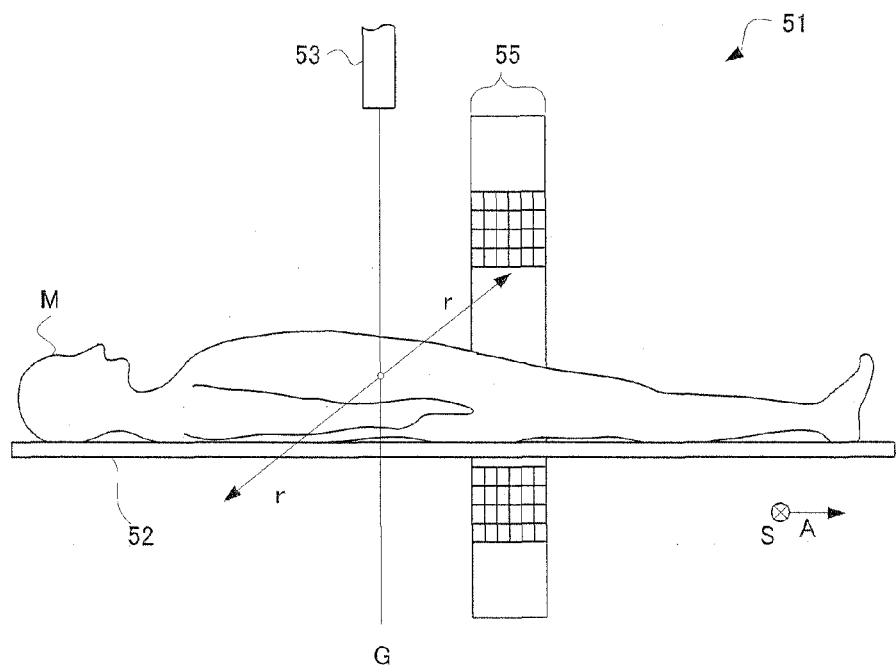
FIG. 16 is a sectional view illustrating the construction of the conventional particle radiotherapy apparatus.

Moreover, according to the construction in Embodiment 1, annihilation gamma ray pairs are detected with the single elliptic detector ring 12. Then, the elliptic detector ring 12 will detect annihilation gamma ray pairs occurring in its interior. In other words, all annihilation gamma ray pairs will impinge on the elliptic detector ring 12 at substantially right angles. This inhibits the lowering of the sensitivity for detection described using FIG. 15.

According to the construction in Embodiment 1, the particle radiotherapy apparatus 9 is provided which can introduce the patient M with increased reliability. That is, the patient M is introduced into the tilted elliptic detector ring 12. If the elliptic detector ring 12 has an elliptic shape at this time, it is possible to prevent the elliptic detector ring 12 and top board 10 from approaching each other due to tilting of the elliptic detector ring 12 relative to the top board 10. In other words, the elliptic detector ring 12 according to the construction in Embodiment 1 can be given an elliptical shape extending to both sides to avoid interference with the top board 10.

Embodiment 2

Next, a particle radiotherapy apparatus 9 according to Embodiment 2 will be described. While Embodiment 2 provides substantially the same construction as Embodiment 1, it has a unique construction in place of the first coupling member 22a and second coupling member 22b in Embodiment 1.

Figure 9:
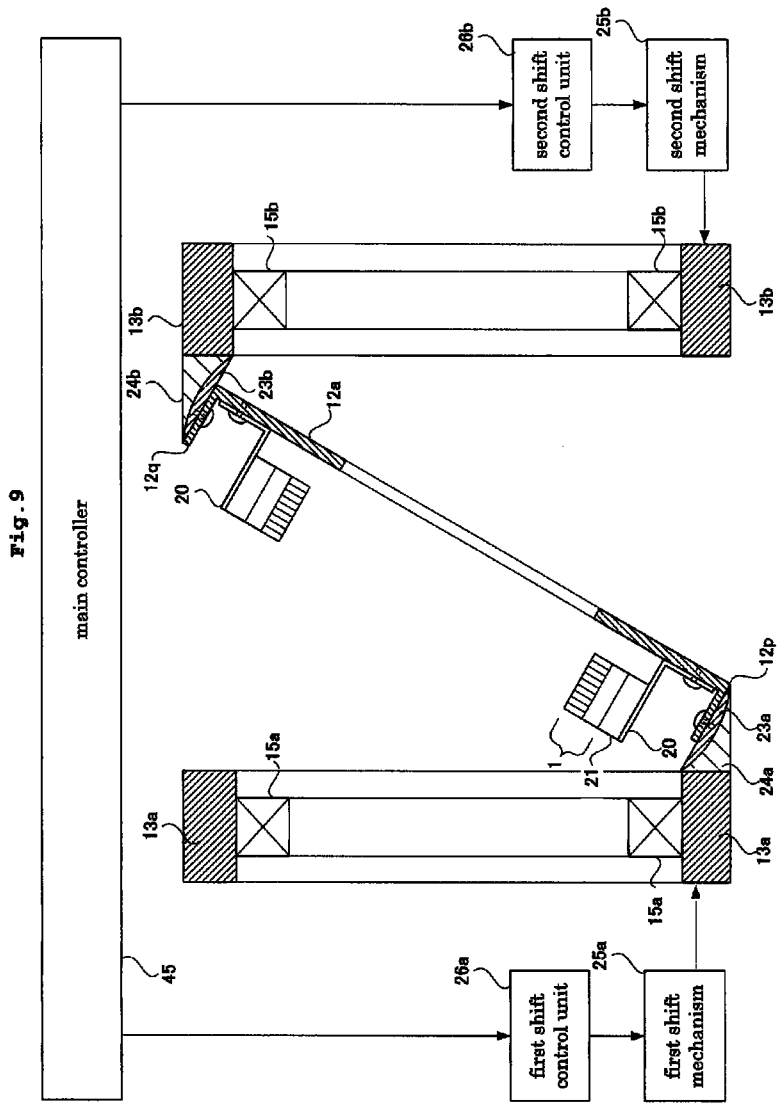
FIG. 9 is a sectional view illustrating a construction of a particle radiotherapy apparatus according Embodiment 2.
Figure 13:
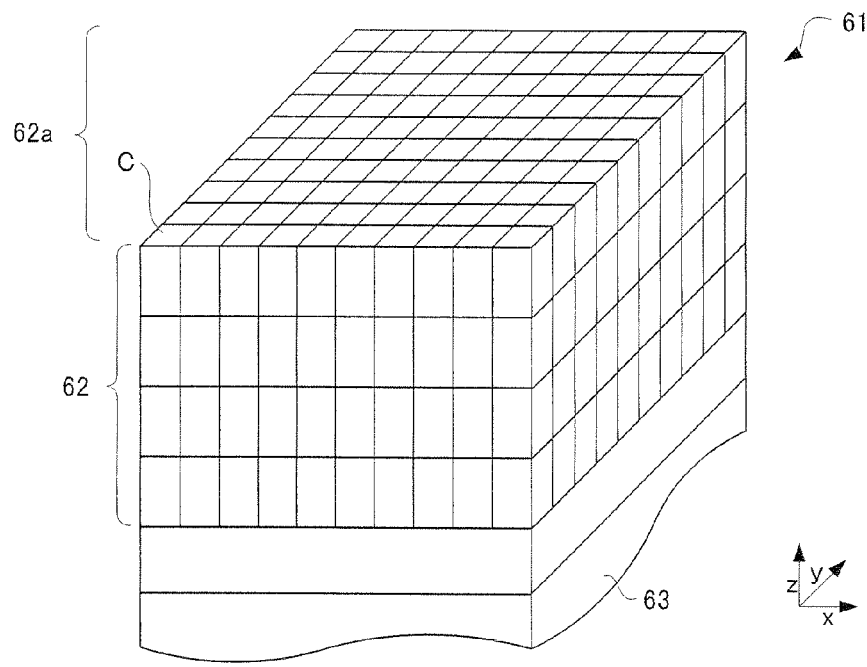
FIG. 13 is a perspective view illustrating the construction of the conventional particle radiotherapy apparatus.
Figure 14:
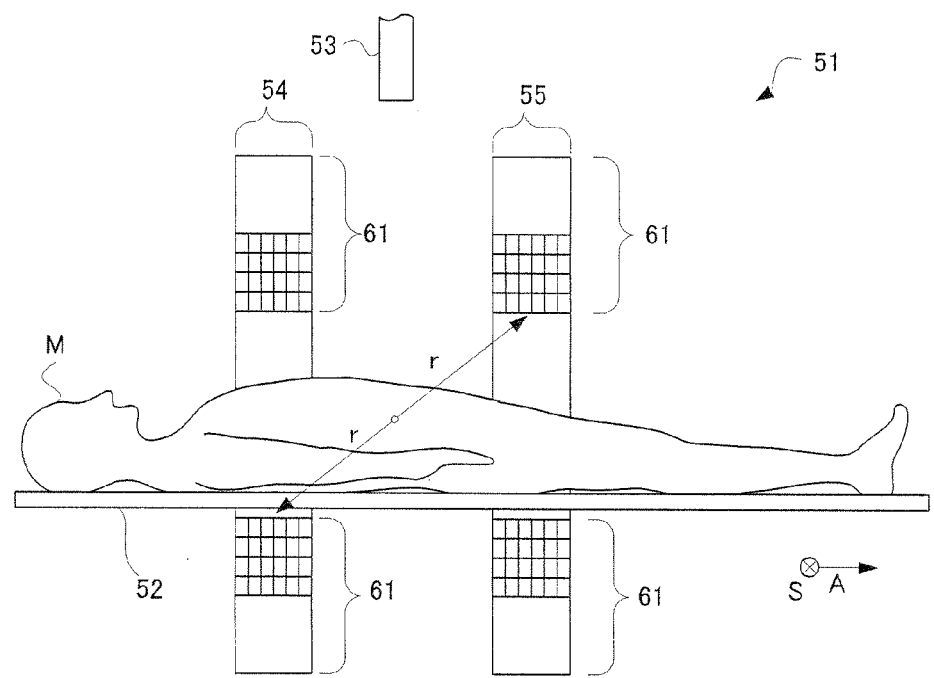
FIG. 14 is a sectional view illustrating the construction of the conventional particle radiotherapy apparatus.

FIG. 9 is a sectional view illustrating the construction of the particle radiotherapy apparatus according to Embodiment 2. As shown in FIG. 9, the elliptic detector ring 12 has a projection projecting in L-shape from a side surface at one end 12p thereof, and the projection is fixed to a first slide member 23a. And a first rail member 24a is in contact with the first slide member 23a, wherein the first slide member 23a and first rail member 24a are slidable. This sliding is caused by a first shift mechanism 25a. The first shift mechanism 25a is controlled by a first shift control unit 26a. The first rail member 24a is fixed to the first ring 13a. The first shift mechanism corresponds to the first shifting device in this invention.

Similarly, the elliptic detector ring 12 has a projection projecting in L-shape from a side surface at the other end 12q thereof, and the projection is fixed to a second slide member 23b. And a second rail member 24b is in contact with the second slide member 23b, wherein the second slide member 23b and second rail member 24b are slidable. This sliding is caused by a second shift mechanism 25b. The second shift mechanism 25b is controlled by a second shift control unit 26b. The second rail member 24b is fixed to the second ring 13b. The second shift mechanism corresponds to the second shifting device in this invention.

Specifically, the first shift mechanism 25a is disposed in a position between the one end 12p of the elliptic detector ring 12 and the first ring 13a, and moves the one end 12p forward and backward relative to the second ring 13b and along an arcuate locus. Similarly, the second shift mechanism 25b is disposed in a position between the other end 12q of the elliptic detector ring 12 and the second ring 13b, and moves the other end 12q forward and backward relative to the first ring 13a and along an arcuate locus.

Next, tilting of the elliptic detector ring 12 which is a characteristic feature of Embodiment 2 will be described. Although, in Embodiment 1, the tilt angle of the elliptic detector ring 12 relative to the first ring 13a is constant, it is variable in Embodiment 2.

FIG. 10 is a schematic view illustrating changes in the tilt angle of the elliptic detector ring according to Embodiment 2. The first shift mechanism 25a and second shift mechanism 25b change the elliptic detector ring 12 from a state in FIG. 10 (a) to a state in FIG. 10 (b). At this time, the one end 12p is moved to follow the arcuate locus in a direction away from the second ring 13b. In connection with this, the other end 12q is moved to follow the arcuate locus in a direction away from the first ring 13a.

The first shift mechanism 25a and second shift mechanism 25b change the elliptic detector ring 12 from the state in FIG. 10 (b) to the state in FIG. 10 (a). At this time, the one end 12p is moved to follow the arcuate locus in a direction toward the second ring 13b. In connection with this, the other end 12q is moved to follow the arcuate locus in a direction toward the first ring 13a.

That is to say, the first shift mechanism 25a and second shift mechanism 25b cause the elliptic detector ring 12 to make a tilting movement relative to the first ring 13a, about a middle point R of a line segment extending between the one end 12p and the other end 12q of the elliptic detector ring 12.

Next, operation of the particle radiotherapy apparatus 9 according to Embodiment 2 will be described. It is substantially the same as the description of operation of Embodiment 1, but is different in the following point. That is, before reaching the emitting step S3 of Embodiment 1, the elliptic detector ring 12 is tilted relative to the first ring 13a. This provides a larger variety of the positional relationship between the elliptic detector ring 12 and the patient M than the construction described in Embodiment 1, thereby to increase the possibility of detecting an annihilation gamma ray pair in a state of good S/N ratio. The reason why changing the positional relationship between the elliptic detector ring 12 and the patient M results in a good S/N ratio has already been described.

The construction in Embodiment 2 may execute the emitting step S3 while changing the tilt of the elliptic detector ring 12 relative to the first ring 13a. Further, the construction in Embodiment 2 may execute the emitting step S3 while changing the tilt of the elliptic detector ring 12 relative to the first ring 13a, and while rotating the elliptic detector ring 12 about base axis C.

Next, data processing of the particle radiotherapy apparatus 9 according to Embodiment 2 will be described. It may be mentioned as a characteristic feature of the construction in Embodiment 2 that detection data outputted from the elliptic detector ring 12 includes information on a tilting direction and a tilt angle of the elliptic detector ring 12 relative to the first ring 13a. When the elliptic detector ring 12 is tilted relative to the first ring 13a, it will change the relative positional relationship between the elliptic detector ring 12 and the patient M. Then, it will be impossible to determine where annihilation gamma rays have generated. However, according to the construction in Embodiment 2, a correction to incline the LOR virtually relative to the first ring 13a is carried out based on the information included in the detection data on the tilting direction and tilt angle relative to the first ring 13a of the elliptic detector ring 12. Therefore, the data outputted from the LOR correcting unit 36 is free from the influence of the change in the tilt relative to the first ring 13a of the elliptic detector ring 12.

As described above, according to the construction in Embodiment 2, the particle radiotherapy apparatus 9 provided has high sensitivity for detecting annihilation gamma rays. It is predicted that various nuclides are generated at points inside the body of the patient M where the particle beam lost energy. The energies and characteristics of the radiation released by decay thereof are varied. It is possible that single photons which are not annihilation gamma ray pairs are released. Such single photons may be detected by the elliptic detector ring 12. These cause noise when imaging positions of action of the particle beam using the annihilation gamma ray pairs. However, according to the construction in Embodiment 1, the rotating angle of the elliptic detector ring 12 can be optimized. Specifically, the particle beam may be emitted in a state of a desired rotating angle of the elliptic detector ring 12 being maintained.

According to the construction in Embodiment 2, the particle radiotherapy apparatus 9 provided has a still higher sensitivity for detecting annihilation gamma rays. It is desirable to render the positional relationship between the top board 10 and elliptic detector ring 12 freely changeable in order to remove the influence of noise as much as possible when imaging an action position of a particle beam using annihilation gamma ray pairs. According to the construction in Embodiment 1, not only the rotating angle relative to the top board 10 of the elliptic detector ring 12, but the tilt angle relative to the top board 10 of the elliptic detector ring 12 also can be changed. This provides an increased degree of freedom for changing the positional relationship between the top board 10 and elliptic detector ring 12, thereby realizing high sensitivity for detecting annihilation gamma rays.

And according to the construction in Embodiment 2, tilting of the elliptic detector ring 12, including also its direction, can be optimized. Specifically, it may be constructed to emit particle beams while tilting the elliptic detector ring 12, in order to determine a positional relationship between the top board 10 and elliptic detector ring 12 producing little noise and well suited for imaging. When a desired tilt of the elliptic detector ring 12 is known, particle beams may be emitted in a state of the tilt angle being maintained.

Where the elliptic detector ring 12 is constructed tiltable, examination can be carried out reliably regardless of the physique of the patient M. In the case of the patient M being obese, if the elliptic detector ring 12 can be tilted, a tilt angle relative to the first ring 13a of the elliptic detector ring 12 can be selected to avoid interference with the patient M.

This invention is not limited to the foregoing constructions, but may be modified as follows:

(1) The construction in Embodiment 1 described above relates to particle radiotherapy which emits a particle beam to the patient M. The particle radiotherapy apparatus 9 of this invention can be used also as an ordinary PET (Positron Emission Tomography) apparatus. That is, the patient M is medicated with a radioactive substance labeled with a positron emission type radioisotope, and a distribution thereof inside the patient M can be imaged.

(2) The scintillator crystals in each foregoing embodiment are formed of LYSO. In this invention, the scintillator crystals may be formed of other materials such as GSO ($Gd_2SiO_5$). This modification can provide a radiation detector manufacturing method that can provide less expensive radiation detectors.

(3) In each foregoing embodiment, the scintillator has four scintillator crystal layers. This invention is not limited to this. For example, a scintillator formed of one scintillator crystal layer may be applied to this invention. In addition, the number of scintillator crystal layers can be adjusted freely according to the use of the radiation detectors.

(4) In each foregoing embodiment, the fluorescence detector is in form of a photomultiplier tube. This invention is not limited to this. Instead of the photomultiplier tube, a photodiode, an avalanche photodiode or the like may be used.

(5) In each foregoing embodiment, as shown in FIG. 11, for example, the top board 10 may have a bore 10a for passage of a particle beam. The top board 10 may be halved into a first fragment 10b and a second fragment 10c, with a slit 10d formed between the first fragment 10b and second fragment 10c for passage of the particle beam. With this construction, the particle beam will be emitted reliably to the patient M without passing through the top board 10.

INDUSTRIAL UTILITY

As described above, this invention is suitable for medical radiographic apparatus.

The invention claimed is:

1. A particle radiotherapy apparatus comprising a detector ring with an annular arrangement of radiation detectors that are formed by laminating, in one direction, a scintillator with a plane of incidence for receiving radiation and converting the radiation into fluorescence, a light guide for receiving and transmitting the fluorescence, and a photodetector for detecting the fluorescence, and comprising, in addition thereto, an elongated top board inserted in an opening of the detector ring, and a particle beam emitting device for emitting a particle beam, the particle radiotherapy apparatus further comprising:

a first ring having a central axis corresponding to a predetermined axis parallel to a direction of extension of the top board;

a second ring having a central axis corresponding to the predetermined axis;

a ring rotating device for rotating the first ring and the second ring about the predetermined axis; and a ring rotation control device for controlling the ring rotating device;

wherein one end of the detector ring is supported by the first ring;

the detector ring is tilted relative to the first ring, and extends from the one end toward the second ring, traversing the top board;

the other end of the detector ring is supported by the second ring; and the detector ring makes rotating movement relative to the top board, in a state of being tilted relative to the first ring, with rotation of the first ring and the second ring.

2. The particle radiotherapy apparatus according to claim 1, wherein the detector ring has an elliptic shape with a long axis consisting of a line segment extending between the one end and the other end thereof.

3. The particle radiotherapy apparatus according to claim 2, wherein the detector ring is arranged to detect radiation resulting from the particle beam, after being rotated by the ring rotating device and in a state of its rotating angle being maintained.

4. The particle radiotherapy apparatus according to claim 2, further comprising:

a first shifting device disposed in a position between the one end of the detector ring and the first ring, for moving the one end forward and backward relative to the second ring and along an arcuate locus;

a first shift control device for controlling this;

a second shifting device disposed in a position between the other end of the detector ring and the second ring, for moving the other end forward and backward relative to the first ring and along an arcuate locus; and a second shift control device for controlling this;

wherein the first shifting device and the second shifting device are arranged to tilt the detector ring relative to the first ring about a middle point of a line segment extending between the one end and the other end.

5. The particle radiotherapy apparatus according to claim 1, wherein the detector ring is arranged to detect radiation resulting from the particle beam, after being rotated by the ring rotating device and in a state of its rotating angle being maintained.

6. The particle radiotherapy apparatus according to claim 5, further comprising:

a first shifting device disposed in a position between the one end of the detector ring and the first ring, for moving the one end forward and backward relative to the second ring and along an arcuate locus;

a first shift control device for controlling this;

a second shifting device disposed in a position between the other end of the detector ring and the second ring, for moving the other end forward and backward relative to the first ring and along an arcuate locus; and a second shift control device for controlling this;

wherein the first shifting device and the second shifting device are arranged to tilt the detector ring relative to the first ring about a middle point of a line segment extending between the one end and the other end.

7. The particle radiotherapy apparatus according to claim 1, further comprising:

a first shifting device disposed in a position between the one end of the detector ring and the first ring, for moving the one end forward and backward relative to the second ring and along an arcuate locus;

a first shift control device for controlling this;

a second shifting device disposed in a position between the other end of the detector ring and the second ring, for moving the other end forward and backward relative to the first ring and along an arcuate locus; and a second shift control device for controlling this;

wherein the first shifting device and the second shifting device are arranged to tilt the detector ring relative to the first ring about a middle point of a line segment extending between the one end and the other end.

8. The particle radiotherapy apparatus according to claim 7, wherein the detector ring is arranged to detect radiation resulting from the particle beam while being tilted by the first shifting device and the second shifting device.

9. The particle radiotherapy apparatus according to claim 7, wherein the detector ring is arranged to detect radiation resulting from the particle beam, after being tilted by the first shifting device and the second shifting device and in a state of its tilt angle being maintained.

* * * * *